(12) United States Patent
Kim et al.

(10) Patent No.: US 8,084,654 B2
(45) Date of Patent: Dec. 27, 2011

(54) MANUFACTURING PROCESS FOR IODINATED AROMATIC COMPOUNDS

(75) Inventors: Han Seok Kim, Gyeonggi-do (KR); Jong In Lee, Gyeonggi-do (KR); Il Hoon Cha, Gyeonggi-do (KR); Yoon Seo Lee, Gyeonggi-do (KR)

(73) Assignee: SK Chemicals Co., Ltd., Suwon (KR)

( * ) Notice: Subject to any disclaimer, the term of this patent is extended or adjusted under 35 U.S.C. 154(b) by 0 days.

(21) Appl. No.: 12/663,625

(22) PCT Filed: Oct. 23, 2007

(86) PCT No.: PCT/KR2007/005227
§ 371 (c)(1),
(2), (4) Date: Dec. 8, 2009

(87) PCT Pub. No.: WO2009/054555
PCT Pub. Date: Apr. 30, 2009

(65) Prior Publication Data
US 2010/0185031 A1    Jul. 22, 2010

(51) Int. Cl.
*C07C 22/00* (2006.01)
(52) U.S. Cl. ........ 570/183; 570/203; 570/206; 570/211; 570/182
(58) Field of Classification Search .................. None
See application file for complete search history.

(56) References Cited

U.S. PATENT DOCUMENTS

| 4,746,758 A |   | 5/1988  | Rule et al.     |         |
|-------------|---|---------|-----------------|---------|
| 4,776,938 A |   | 10/1988 | Abe et al.      |         |
| 4,786,713 A |   | 11/1988 | Rule et al.     |         |
| 4,788,353 A | * | 11/1988 | Paparatto et al.| 570/203 |
| 4,861,929 A | * | 8/1989  | Miyake et al.   | 570/209 |
| 4,895,992 A | * | 1/1990  | Rule et al.     | 570/203 |
| 2006/0161028 A1 | | 7/2006 | Hidaka et al.  |         |

FOREIGN PATENT DOCUMENTS

| JP | 07330665 A | 12/1995 |
|----|------------|---------|
| WO | WO 89/08631 | 9/1989 |

* cited by examiner

*Primary Examiner* — Sudhakar Katakam
(74) *Attorney, Agent, or Firm* — McDermott Will & Emery LLP

(57) ABSTRACT

Disclosed is a method for preparing an iodinated aromatic compound. More specifically, disclosed is a method of preparing an iodinated aromatic compound by iodinating an aromatic compound in the presence of oxygen over a zeolite catalyst, in which the aromatic compound and its monoiodo compound, as raw materials, are allowed to react with iodine. In comparison with a method in which only the aromatic compound is used as a raw material without adding the monoiodo compound, the disclosed method can increase the productivity of diiodo compounds and the selectivity to a p-diiodo compound and, at the same time, suppress side reactions, thus lengthening the life span of the catalyst.

2 Claims, 4 Drawing Sheets

US 8,084,654 B2

MANUFACTURING PROCESS FOR IODINATED AROMATIC COMPOUNDS

CROSS REFERENCE TO PRIOR APPLICATIONS

This application is the U.S. National Phase Application under 35 U.S.C. §371 of International Patent Application No. PCT/KR2007/005227 filed Oct. 23, 2007, which is hereby incorporated by reference in its entirety. The International Application was published in English as WO 2009/054555 A1 on Apr. 30, 2009.

TECHNICAL FIELD

The present invention relates to a method for preparing an iodinated aromatic compound, and more particularly to a method of preparing an iodinated aromatic compound by iodinating an aromatic compound in the presence of oxygen using a zeolite catalyst, in which the aromatic compound and its monoiodo compound, as raw materials, are allowed to react with iodine.

BACKGROUND ART

Technology of preparing halogenated aromatic compounds by aromatic compounds such as benzene or naphthalene to react with halogen (bromine, chlorine, iodine, etc) has been used in various commercial fields.

Typically, p-dichlorobenzene, which is prepared through the reaction of benzene with chlorine, is used as a raw material for preparing engineering plastic PPS (polyphenylene sulfide). Technology of preparing PPS by allowing p-dichlorobenzene to react with sodium sulfide in an N-methyl pyrrolidone solvent is known as the Macallum process, and PPS is currently commercially produced through the Macallum process. However, because it is difficult to obtain a high-molecular-weight polymer only through the Macallum process, a curing process, as a post-process, is carried out to obtain the high-molecular-weight polymer, and PPS obtained through the curing process has a disadvantage in that it becomes brittle due to a crosslinking reaction or the like. Also, metal salts, such as sodium chloride (NaCl), are necessarily produced as reaction byproducts in the polymerization process, and cause serious problems in terms of the economic efficiency of commercial processes and the physical properties of the polymer.

As methods which can fundamentally eliminate the production of metal salts and enable linear polymers to be obtained, U.S. Pat. Nos. 4,746,758 and 4,786,713 and related patents suggest methods of melt-polymerizing p-diiodobenzene with sulfur.

Also, U.S. Pat. Nos. 4,778,938 and 4,746,758 disclose methods of preparing p-diiodobenzene by allowing benzene to react with iodine in the presence of oxygen over a zeolite catalyst. These patents disclose that conversion is high, the selectivity to a p-diiodo compound, which is commercially useful, is high, and the oxidation of benzene or naphthalene as a raw material can be minimized.

However, in order to make this iodination technology commercially more useful, it is preferable to further increase the productivity of diiodo compounds and the selectivity to a p-diiodo compound. Also, said patents disclose that carbon deposits are produced due to the combustion of raw material and that the activity of the catalyst is reduced due to the carbon deposits. Furthermore, the carbon deposits thus produced or multi-iodinated high molecular impurities not only deactivate the catalyst, but also remain in the iodinated product, thus causing serious problems in a subsequent purification process.

DISCLOSURE

Technical Problem

The present inventors have conducted studies to solve the above-described problems occurring in the prior art and, as a result, found that, when an aromatic compound, such as benzene or naphthalene, and its monoiodo compound, as raw materials, are allowed to react with iodine, the productivity of diiodo compounds and the selectivity to a p-diiodo compound can be increased, and the life span of a catalyst can be significantly increased, thereby completing the present invention.

Therefore, it is an object of the present invention to provide a method for preparing an iodinated aromatic compound, which can minimize the deactivation of a catalyst, increase the productivity of diiodo compounds from an aromatic compound and the selectivity to a p-diiodo compound and, at the same time, suppress side reactions.

Technical Solution

To achieve the above object, the present invention provides a method of preparing an iodinated aromatic compound by iodinating an aromatic compound in the presence of oxygen over a zeolite catalyst, in which the aromatic compound and its monoiodo compound, as raw materials, are allowed to react with iodine.

Advantageous Effects

According to the present invention, an aromatic compound and its monoiodo compound, as raw materials, are allowed to react with iodine, whereby the productivity of diiodo compounds and the selectivity to a p-diiodo compound can be increased and, at the same time, side reactions can be suppressed, thus lengthening the life span of a catalyst.

DESCRIPTION OF IMPORTANT REFERENCE NUMERALS USED IN THE FIGURES

Figure 1:
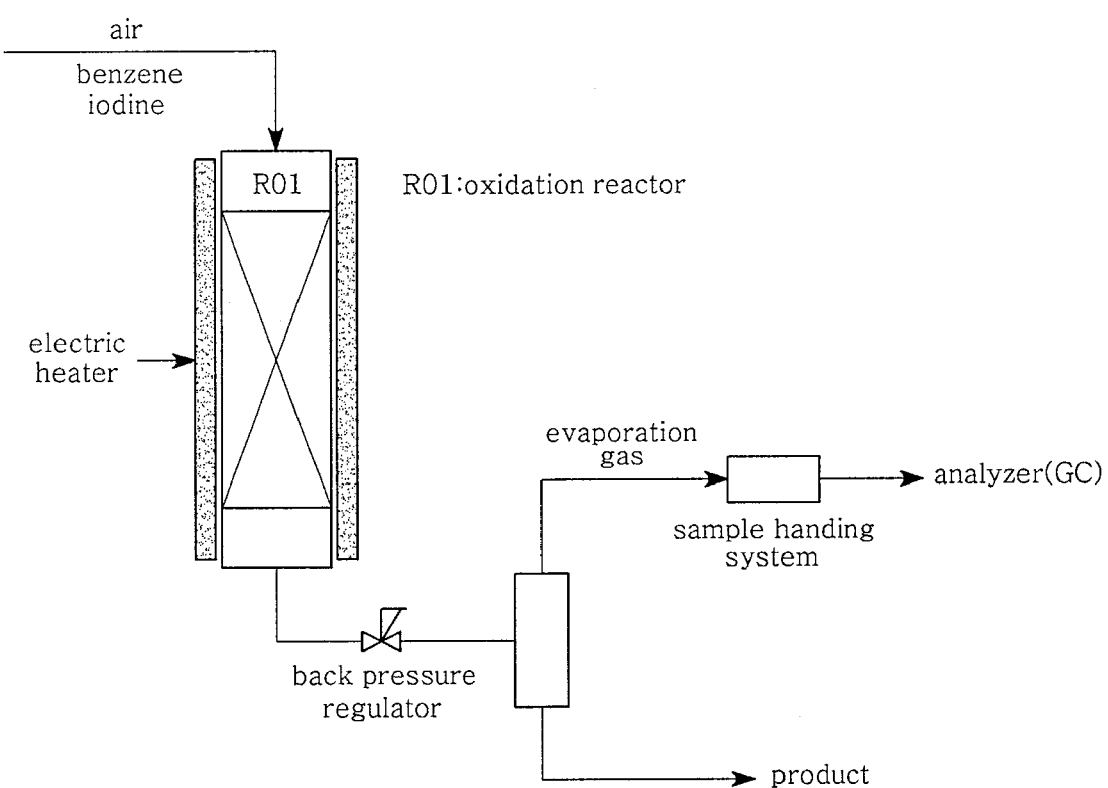
FIG. 1 is a schematic diagram showing a system and process for preparing an iodinated compound according to Comparative Example 1.

R01: an iodination reactor (packed with 230 ml of an Na-13X zeolite catalyst and equipped with an electric heater);

C10: distillation column 1 for removing water and benzene from a reaction product;

C20: distillation column 2 for separating and recycling monoiodobenzene and iodine from a reaction product;

C30: distillation column 3 for separating diiodobenzene through the top of the column and removing high-boiling-point substances, including triiodo compounds, through the bottom of the column;

back pressure regulator: serving to regulate reaction pressure and enabling a pressurized reaction to be carried out;

sample handling system: for removing vapor from gas in order to protect an analyzer in a post-process; and GC (gas chromatography): for measuring the content of carbon dioxide in gas.

BEST MODE

Hereinafter, the present invention will be described in detail.

As described above, the present invention relates to a method for iodinating an aromatic compound in the presence of oxygen over a zeolite catalyst, wherein an aromatic compound and its monoiodo compound are used as raw materials, whereby the deactivation of the catalyst can be minimized, the productivity of diiodo compounds and the selectivity to a p-diiodo compound can be increased and, at the same time, side reactions can be suppressed, thus lengthening the life span of the catalyst.

Also, in the present invention, it is possible to recycle the monoiodo compound and iodine by separating and purifying the reaction product, obtained according to the above method, through distillation.

In the present invention, as the catalyst for the iodination reaction, an Na-13X zeolite catalyst, which is commercially widely used, was used. In the present invention, various catalysts, including Y-type, ZSM5 and K-13X, were used to carry out the iodination of the aromatic compound, but the Na-13X catalyst was found to be most useful. It could be seen that the K-13X zeolite catalyst had low usefulness, such that the conversion of the aromatic compound and iodine was not greater than 50%, and the usefulness of the remaining catalysts was also lower than that of the Na-13X catalyst.

It is known that the iodination of aromatic compounds over a zeolite catalyst occurs over a wide temperature range of 200-400° C. In the present invention, the iodination of aromatic compounds was examined at various reaction temperatures and, as a result, it could be seen that, as the reaction temperature was increased, the conversion of raw materials (aromatics and iodine) was increased, but the selectivity to the p-diiodo compound, which is considered to be commercially most valuable, and the productivity of the diiodo compounds, were decreased. Meanwhile, the iodination reaction can be carried out at a wide range of reaction pressure, and it could be seen that an increase in the reaction pressure led to an increase in the efficiency of the iodination reaction.

Meanwhile, hydroiodic acid, which is produced during the iodination reaction, should be oxidized to iodine, which can participate in the reaction. For this reason, the presence of oxygen in the reaction is considered to be essential. If oxygen is not present or the amount thereof is smaller than the amount of hydroiodic acid, hydroiodic acid will form azeotropes with water, generated during the reaction, and thus it will adversely affect a purification process after the reaction, and in addition, will severely corrode equipment due to its strong oxidation action. Accordingly, it can be seen that oxygen in an amount equal to or greater than the number of moles of iodine, which is used in the reaction, is required.

The molar ratio between the aromatic compound and iodine, which are used as raw materials, can vary. It can be seen that, as the amount of iodine was increased, the productivity of multi-iodinated aromatics was increased, but the conversion of iodine was decreased. However, if the ratio of the aromatic compound to the iodo compound is increased in order to increase the conversion of iodine, the conversion of iodine can be increased, but the productivity of the diiodo compounds will be reduced. For this reason, the ratio should be suitably adjusted according to the intended use of the reaction product.

Aromatic compounds, such as benzene or naphthalene, are converted to oxides, such as carbon dioxide, through an oxidation reaction, when they are in a condition of high temperatures in the presence of oxygen. This indicates the loss of raw materials. Herein, carbon dioxide is produced through complete oxidation, and can also form carbon deposits through incomplete oxidation or carbonization. The carbon deposits thus formed reduce the activity of the catalyst, thus shortening the life span of the catalyst.

According to the present invention, the productivity of diiodo compounds and the selectivity to a p-diiodo compound can be increased through the use of an aromatic compound and its monoiodo compound as raw materials. Also, according to the method suggested in the present invention, the production of carbon dioxide and carbon deposits can be minimized, and thus the life span of the catalyst can be significantly lengthened, and high-quality iodinated compounds can be obtained.

According to the present invention, the aromatic compound is preferably selected from the group consisting of benzene, naphthalene and biphenyl, and the monoiodo compound is preferably selected from the group consisting of monoiodobenzene, monoiodonaphthalene and monoiodobiphenyl, but the scope of the present invention is not limited thereto.

Figure 4:
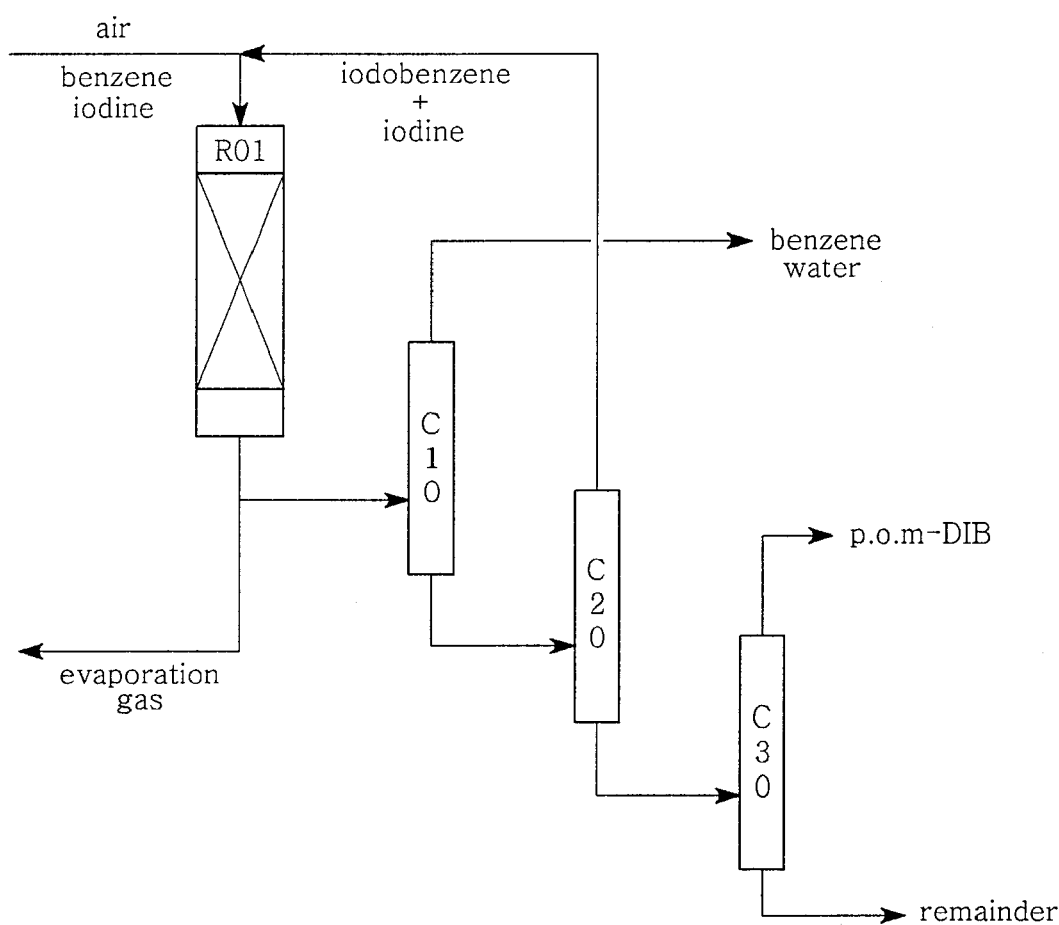
FIG. 4 is a schematic diagram showing a system and process for preparing an iodinated compound according to Example 6, in which the separation and recycling of a monoiodo compound and iodine are carried out.

Also, although the monoiodo compound can be prepared or purchased for use in the present invention, it is more efficient to separate and purify a monoiodo compound from the iodinated reaction product by distillation and recycle the separated compound, as shown in FIG. 4. Specifically, as shown in FIG. 4, the method of the present invention can be efficiently embodied by removing benzene and water in distillation column 1 (C10), separating monoiodobenzene and iodine through the top of distillation column 2 (C20), and introducing the separated materials into a reactor (R01).

In order to prove the effect of the present invention, the concept of the terms used in Comparative Examples and Examples, which are described later, will now be described. "Aromatic/iodine ratio" in reaction conditions indicates the molar ratio between the aromatic compound and the iodine that is used. When a diiodo compound is to be prepared, benzene should react with one mole of iodine (two iodine atoms). Thus, the aromatic/iodine ratio is defined by the following Math Figure 1:

$$\text{Aromatic/iodine} = (\text{moles of benzene} \times 2) + (\text{moles of monoiodobenzene})/\text{moles of iodine} \times 2 \quad \text{[Math Figure 1]}$$

The concept of the terms for examining a reaction product and the efficiency of a reaction process will now be described. The productivity of p-diiodobenzene (p-DIB) is defined as the production rate of p-diiodobenzene per unit volume of a catalyst per unit time, and is expressed in a unit of g/l·hr. The conversion of iodine and benzene is obtained by dividing the amount of iodine and benzene, converted to the reaction product, by the amount of iodine and benzene that is introduced, and then expressing the ratio as a percentage (%).

Figure 2:
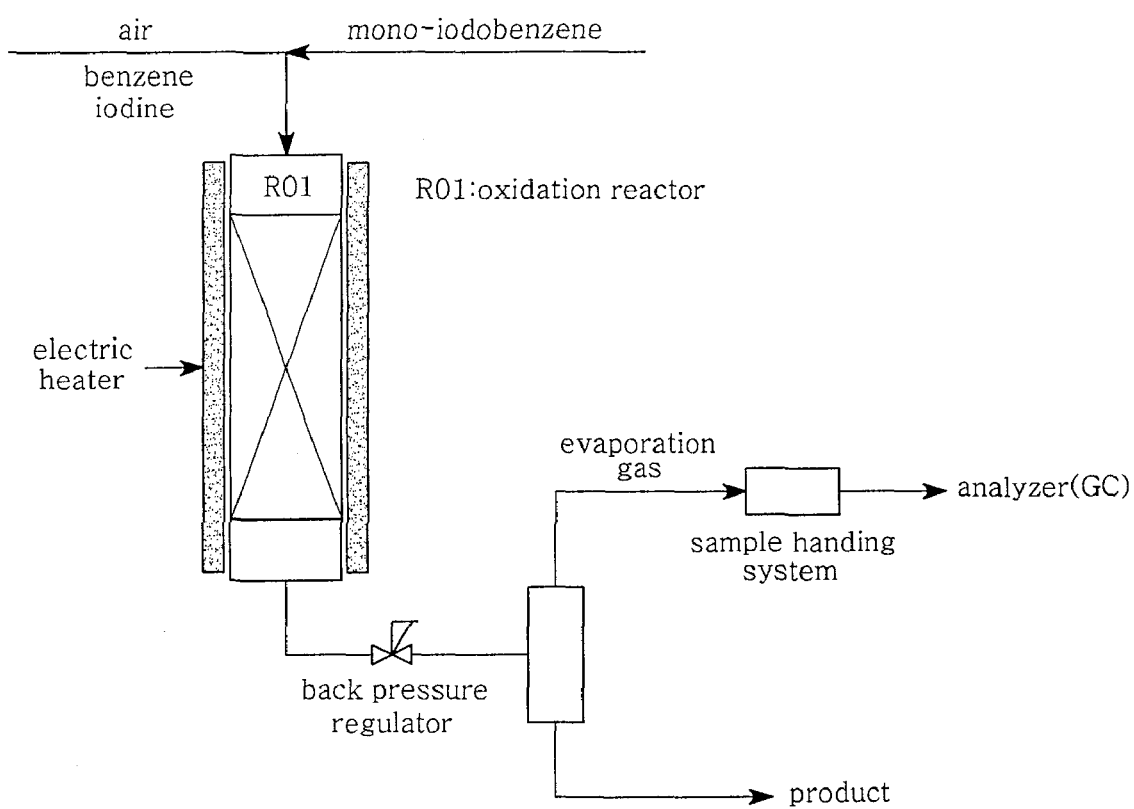
FIG. 2 is a schematic diagram showing a system and process for preparing an iodinated compound according to Examples 1 to 3.

Iodinated benzenes produced through the iodination reaction can be classified into the following compounds: mono-iodobenzene, obtained by reaction with one iodine atom; di-iodobenzene, obtained by reaction with two iodine atoms; and tri-iodobenzene, obtained by reaction with three iodine atoms. Among them, di-iodobenzene (DIB) and tri-iodobenzene (TIB) may each have three isomers. That is, for di-iodobenzenes, three isomers, including p-, o- and m-diiodobenzenes, are produced by the iodination reaction. Herein, total diiodobenzene (DIB) refers to the total of the weight percentages of p-, o- and m-diiodobenzenes contained in the reaction product, and is defined by the following Math Figure 2:

$$\text{Total DIB} = (p+m+o\ \text{DIB})/(\text{Product}) \times 100 \quad [\text{Math Figure 2}]$$

Figure 3:
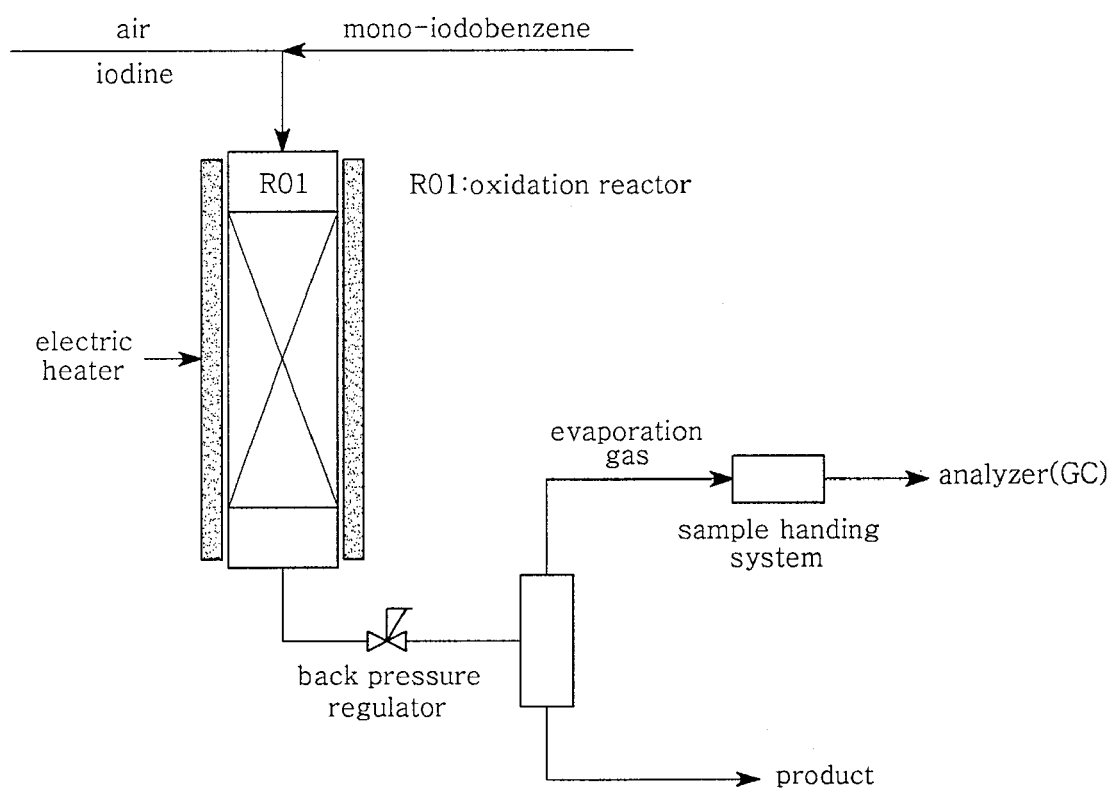
FIG. 3 is a schematic diagram showing a system and process for preparing an iodinated compound according to Example 4.

Meanwhile, selectivity is expressed as a weight percentage of the concentration of the p-isomer among three diiodobenzenes contained in the reaction product, and is defined by the following Math Figure 3:

$$\text{Selectivity} = (p\text{-DIB})/(p+m+o\ \text{DIB}) \times 100 \quad [\text{Math Figure 3}]$$

According to the present invention, the p-diiodo compound, which is commercially highly valuable, can be prepared at high efficiency, and this high-efficiency preparation is made possible when the total DIB and the selectivity to the p-diiodo compound are high.

MODE FOR INVENTION

Hereinafter, the present invention will be described in further detail with reference to the following examples, but the scope of the present invention is not limited to these examples.

Comparative Example 1

In the system shown in FIG. 1, benzene (26.4 g/hr) and iodine (42.9 g/hr) were fed into a reactor without adding monoiodobenzene, and were subjected to a continuous iodination process under conditions of a reaction temperature of 280° C. and atmospheric pressure. 24 hours after the reaction conditions were reached, sampling and analysis were performed. The experimental conditions and results are shown in Table 1 below.

Example 1

In the system shown in FIG. 2, benzene (6.6 g/hr), monoiodobenzene (48.4 g/hr) and iodine (25.8 g/hr) were fed into a reactor and subjected to an iodination reaction under the same conditions as in Comparative Example 1. The experimental conditions and results are shown in Table 1 below.

Example 2

In the system shown in FIG. 2, benzene (16.5 g/hr), monoiodobenzene (38.5 g/hr) and iodine (38.8 g/hr) were fed into a reactor and subjected to an iodination reaction under the same conditions as in Comparative Example 1. The experimental conditions and results are shown in Table 1 below.

Example 3

In the system shown in FIG. 2, benzene (27.5 g/hr), monoiodobenzene (27.5 g/hr) and iodine (53.2 g/hr) were fed into a reactor and subjected to an iodination reaction in the same conditions as in Comparative Example 1. The experimental conditions and results are shown in Table 1 below.

Example 4

In the system shown in FIG. 3, monoiodobenzene (55 g/hr) and iodine (17.1 g/hr) were fed into a reactor without adding benzene, and were subjected to an iodination reaction under the same conditions as in Comparative Example 1. The experimental conditions and results are shown in Table 1 below.

TABLE 1

| | | Comparative Example 1 | Example 1 | Example 2 | Example 3 | Example 4 |
|---|---|---|---|---|---|---|
| Feed conditions | | | | | | |
| Benzene | g/hr | 26.4 | 6.6 | 16.5 | 27.5 | 0 |
| Iodobenzene | g/hr | 0.0 | 48.4 | 38.5 | 27.5 | 55 |
| Iodine | g/hr | 42.9 | 25.8 | 38.8 | 53.2 | 17.1 |
| Aromatic/iodine | Molar ratio | 2.0 | 2.0 | 2.0 | 2.0 | 2.0 |
| $O_2$ | ml/min | 220.0 | 100.0 | 120.0 | 200.0 | 80 |
| Composition of product | | | | | | |
| Benzene | wt % | 9.84 | 3.63 | 7.71 | 9.78 | 0 |
| Iodobenzene | wt % | 44.31 | 38.53 | 44.01 | 44.25 | 45 |
| p-DIB | wt % | 22.99 | 40.47 | 33.96 | 30.78 | 38.97 |
| m-DIB | wt % | 9.21 | 6.76 | 6.21 | 6.88 | 7.84 |
| o-DIB | wt % | 2.92 | 1.88 | 1.98 | 2.54 | 2.12 |
| TIB | wt % | 3.11 | 5.19 | 3.49 | 3.24 | 5.65 |
| Characteristics | | | | | | |
| Productivity of p-DIB | g/l · hr | 69.97 | 123.17 | 103.36 | 93.68 | 118.60 |
| Conversion rate of $I_2$ | % | 91.38 | 88.41 | 90.20 | 90.50 | 92.44 |
| Conversion rate of benzene | % | 73.96 | 61.50 | 67.29 | 75.11 | — |
| Total DIB | wt % | 35.12 | 49.11 | 42.15 | 40.20 | 48.93 |
| Selectivity | % | 66.00 | 83.00 | 80.57 | 77.00 | 80.00 |
| $CO_2$ | % | 2.54 | 0.78 | 0.88 | 1.16 | 0.05 |

As can be seen in Table 1 above, Examples 1 to 3, in which benzene and monoiodobenzene were fed and subjected to iodination, showed excellent results in terms of total DIB and the selectivity to diiodobenzene, compared to Comparative Example 1, in which only benzene was used as a raw material. Results similar thereto could also be observed in Example 4, in which monoiodobenzene was used as the raw material without adding benzene. The productivity of p-DIB was also high, when only monoiodobenzene was used as the raw material or when benzene was used together with monoiodobenzene. Thus, it could be seen that the production of the p-isomers per unit volume of the catalyst was efficiently achieved.

Comparative Example 2

An iodination reaction was carried out in the same manner as in Comparative Example 1, and the product was analyzed 200 hours and 400 hours after the initiation of the reaction.

Example 5

An iodination reaction was carried out in the same manner as in Example 3, and the product was analyzed 200 hours and 400 hours after the initiation of the reaction.

TABLE 2

|  | Conversion rate (%) of $I_2$ | | Black impurities (g) | |
| --- | --- | --- | --- | --- |
|  | 200 hr | 400 hr | 200 hr | 400 hr |
| Comparative Example 2 | 80 | 65 | 1 | 3 |
| Example 5 | 87 | 82 | 0.13 | 0.38 |

As can be seen in Table 2 above, in the case of Comparative Example 2, the conversion of iodine was reduced to 80% after 200 hours and 65% after 400 hours, and the amount of black impurities detected in the product was increased with the passage of time. In the case of Example 5, the conversions of iodine after 200 hours and 400 hours were 87% and 82%, respectively, and the black impurities were detected in significantly small amounts, compared to those of Comparative Example 2. It is considered that the black impurities are carbon deposits contained in the products, and the carbon deposits reduce the activity of the catalyst. This can also be confirmed from the carbon dioxide productions of Comparative Example 1 and Examples 1 to 4, as shown in Table 1 above. In the case where benzene and monoiodobenzene are used, the concentration of carbon dioxide in gas was significantly reduced, compared to the case where only benzene was used as the raw material.

Example 6

Example 6 was carried out in the system shown in FIG. 4. Herein, the melting temperatures of p-, m- and o-diiodobenzenes were 131° C., 36° C. and 27° C., respectively. Thus, although diiodobenzenes are all considered to be in a solid state at room temperature (25° C.), the diiodobenzene recovered from the top of the third distillation column (CO3) was present as a solid-liquid mixture. For this reason, the recovered diiodobenzene was subjected to crystallization and solid-liquid separation and, as a result, it could be separated into a pure p-isomer solid and a solution consisting of 13.1% p-diiodobenzene, 71.5% m-diiodobenzene and 15.4% o-diiodobenzene. By washing the p-isomer solid, white p-diiodobenzene having a purity of more than 99% could be obtained. Also, it could be seen that the three isomers (p-, m- and o-isomers) can be present in the liquid state by forming a eutectic mixture at a temperature lower than the respective melting temperatures.

The invention claimed is:

1. A method of preparing an iodinated aromatic compound by reacting (i) an aromatic compound and a monoiodo analog of the aromatic compound or (ii) a monoiodo aromatic compound, with iodine in the presence of oxygen using a zeolite catalyst to form a p-diiodo aromatic compound, wherein
the oxygen is in an amount equal to or greater than the number of moles of iodine wherein the aromatic compound is one or more selected from the group consisting of benzene and biphenyl, wherein the monoiodo aromatic compound is one or more selected from the group consisting of monoiodobenzene and monoiodobiphenyl.

2. The method of claim 1, wherein the monoiodo aromatic compound and iodine are recycled through the steps of: 1) removing benzene and water from a reaction product; 2) separating the monoiodo aromatic compound and iodine from the reaction product through the top of a column; and 3) recycling by reintroducing the separated monoiodo aromatic compound and iodine into the iodination reactor.

* * * * *